(12) United States Patent
Albertorio et al.

(10) Patent No.: US 8,231,674 B2
(45) Date of Patent: Jul. 31, 2012

(54) BONE-TENDON-BONE SUTURE BUTTON CONSTRUCTS AND METHODS OF TISSUE FIXATION

(75) Inventors: Ricardo Albertorio, Naples, FL (US); Jacob A. Jolly, Naples, FL (US)

(73) Assignee: Arthrex, Inc., Naples, FL (US)

( * ) Notice: Subject to any disclaimer, the term of this patent is extended or adjusted under 35 U.S.C. 154(b) by 120 days.

(21) Appl. No.: 12/813,380

(22) Filed: Jun. 10, 2010

(65) Prior Publication Data

US 2010/0324676 A1 Dec. 23, 2010

Related U.S. Application Data

(60) Provisional application No. 61/218,833, filed on Jun. 19, 2009.

(51) Int. Cl.
*A61F 2/08* (2006.01)
*A61B 17/04* (2006.01)

(52) U.S. Cl. .................... 623/13.14; 606/232

(58) Field of Classification Search ............... 606/232, 606/233, 228, 222, 223, 321, 88; 623/13.11–13.2
See application file for complete search history.

(56) References Cited

U.S. PATENT DOCUMENTS

| | | | | |
|---|---|---|---|---|
| 65,499 A | * | 6/1867 | Miller | 24/115 R |
| 261,501 A | * | 7/1882 | Vandermark | 24/115 R |
| 3,910,281 A | * | 10/1975 | Kletschka et al. | 606/232 |
| 4,708,132 A | * | 11/1987 | Silvestrini | 606/66 |
| 4,901,721 A | * | 2/1990 | Hakki | 606/103 |
| 4,927,421 A | * | 5/1990 | Goble et al. | 606/232 |
| 5,139,520 A | * | 8/1992 | Rosenberg | 606/87 |
| 5,152,790 A | * | 10/1992 | Rosenberg et al. | 623/13.14 |
| 5,211,647 A | * | 5/1993 | Schmieding | 606/104 |
| 5,259,846 A | * | 11/1993 | Granger et al. | 606/224 |
| 5,306,301 A | * | 4/1994 | Graf et al. | 606/232 |
| 5,320,626 A | | 6/1994 | Schmieding | |
| 5,405,352 A | * | 4/1995 | Weston | 606/148 |
| 5,480,961 A | * | 1/1996 | Jiang et al. | 528/220 |
| 5,527,342 A | * | 6/1996 | Pietrzak et al. | 606/232 |
| 5,628,756 A | * | 5/1997 | Barker et al. | 606/139 |
| 5,643,295 A | * | 7/1997 | Yoon | 606/151 |
| 5,645,588 A | * | 7/1997 | Graf et al. | 606/151 |
| 5,665,109 A | * | 9/1997 | Yoon | 606/232 |
| 5,693,060 A | * | 12/1997 | Martin | 606/148 |
| 5,707,395 A | * | 1/1998 | Li | 606/232 |
| 5,728,109 A | * | 3/1998 | Schulze et al. | 606/139 |
| 5,769,894 A | * | 6/1998 | Ferragamo | 606/148 |
| 5,782,864 A | * | 7/1998 | Lizardi | 606/232 |
| 5,879,371 A | * | 3/1999 | Gardiner et al. | 606/224 |
| 5,989,252 A | * | 11/1999 | Fumex | 606/232 |

(Continued)

FOREIGN PATENT DOCUMENTS

EP 0 998 883 A2 5/2000

(Continued)

*Primary Examiner* — Alvin J. Stewart
(74) *Attorney, Agent, or Firm* — Dickstein Shapiro LLP

(57) ABSTRACT

A continuous loop and button construct and technique for ligament repair and fixation, including bone to bone, or soft tissue to bone. The continuous loop, which is attached to the button, is formed of a flexible material and is provided with at least one joined region (a bridged, stitched, bonded or knotted region) to form a closed loop figure-8 construct with proximal and distal openings with respect to the fixation device. The figure-8 construct (either bridged, stitched, bonded or knotted) is adapted for attachment to a bone block of a BTB graft, for example, and used for ligament reconstruction.

8 Claims, 13 Drawing Sheets

U.S. PATENT DOCUMENTS

| | | | | |
|---|---|---|---|---|
| 6,027,523 | A * | 2/2000 | Schmieding | 606/232 |
| 6,056,752 | A * | 5/2000 | Roger | 623/13.12 |
| 6,080,154 | A * | 6/2000 | Reay-Young et al. | 606/60 |
| 6,110,207 | A * | 8/2000 | Eichhorn et al. | 623/13.14 |
| 6,193,754 | B1 * | 2/2001 | Seedhom | 623/13.11 |
| 6,293,961 | B2 * | 9/2001 | Schwartz et al. | 606/232 |
| 6,514,274 | B1 * | 2/2003 | Boucher et al. | 606/232 |
| 6,517,578 | B2 * | 2/2003 | Hein | 623/13.13 |
| 6,527,795 | B1 * | 3/2003 | Lizardi | 606/232 |
| 6,533,802 | B2 * | 3/2003 | Bojarski et al. | 606/232 |
| 6,596,015 | B1 * | 7/2003 | Pitt et al. | 606/232 |
| 6,641,596 | B1 * | 11/2003 | Lizardi | 606/232 |
| 6,761,722 | B2 * | 7/2004 | Cole et al. | 606/74 |
| 6,887,259 | B2 * | 5/2005 | Lizardi | 606/232 |
| 7,077,863 | B2 * | 7/2006 | Schmieding et al. | 623/13.14 |
| 7,235,091 | B2 * | 6/2007 | Thornes | 606/232 |
| 7,329,272 | B2 * | 2/2008 | Burkhart et al. | 606/232 |
| 7,367,978 | B2 * | 5/2008 | Drewry et al. | 606/279 |
| 7,390,332 | B2 * | 6/2008 | Selvitelli et al. | 606/232 |
| 7,410,489 | B2 * | 8/2008 | Dakin et al. | 606/103 |
| 7,455,683 | B2 * | 11/2008 | Geissler et al. | 606/232 |
| 7,530,990 | B2 * | 5/2009 | Perriello et al. | 606/232 |
| 7,572,275 | B2 * | 8/2009 | Fallin et al. | 606/232 |
| 7,582,105 | B2 * | 9/2009 | Kolster | 606/228 |
| 7,591,850 | B2 * | 9/2009 | Cavazzoni | 623/13.11 |
| 7,618,438 | B2 * | 11/2009 | White et al. | 606/232 |
| 7,651,509 | B2 * | 1/2010 | Bojarski et al. | 606/139 |
| 7,658,751 | B2 * | 2/2010 | Stone et al. | 606/232 |
| 7,686,838 | B2 * | 3/2010 | Wolf et al. | 606/325 |
| 7,722,644 | B2 * | 5/2010 | Fallin et al. | 606/232 |
| 7,744,611 | B2 * | 6/2010 | Nguyen et al. | 606/151 |
| 7,776,077 | B2 * | 8/2010 | Kaiser et al. | 606/300 |
| 7,806,909 | B2 * | 10/2010 | Fallin et al. | 606/232 |
| 7,819,898 | B2 * | 10/2010 | Stone et al. | 606/232 |
| 7,846,180 | B2 * | 12/2010 | Cerier | 606/232 |
| 7,857,830 | B2 * | 12/2010 | Stone et al. | 606/232 |
| 7,875,057 | B2 * | 1/2011 | Cook et al. | 606/232 |
| 7,875,058 | B2 * | 1/2011 | Holmes, Jr. | 606/232 |
| 7,887,551 | B2 * | 2/2011 | Bojarski et al. | 606/139 |
| 7,901,431 | B2 * | 3/2011 | Shurnas | 606/232 |
| 7,909,851 | B2 * | 3/2011 | Stone et al. | 606/232 |
| 7,947,053 | B2 * | 5/2011 | McKay et al. | 606/148 |
| 7,959,650 | B2 * | 6/2011 | Kaiser et al. | 606/232 |
| 7,963,973 | B2 * | 6/2011 | Nguyen et al. | 606/153 |
| 7,967,843 | B2 * | 6/2011 | Kaiser et al. | 606/232 |
| 8,052,719 | B2 * | 11/2011 | Paulos | 606/232 |
| 2003/0236555 | A1 * | 12/2003 | Thornes | 606/232 |
| 2004/0015171 | A1 * | 1/2004 | Bojarski et al. | 606/72 |
| 2004/0111101 | A1 * | 6/2004 | Chin | 606/151 |
| 2004/0133238 | A1 * | 7/2004 | Cerier | 606/232 |
| 2004/0199166 | A1 * | 10/2004 | Schmieding et al. | 606/79 |
| 2006/0064126 | A1 * | 3/2006 | Fallin et al. | 606/232 |
| 2007/0225805 | A1 * | 9/2007 | Schmieding | 623/13.14 |
| 2007/0233241 | A1 * | 10/2007 | Graf et al. | 623/13.14 |
| 2007/0239209 | A1 * | 10/2007 | Fallman | 606/232 |
| 2007/0250163 | A1 * | 10/2007 | Cassani | 623/13.17 |
| 2007/0260259 | A1 * | 11/2007 | Fanton et al. | 606/99 |
| 2008/0046009 | A1 * | 2/2008 | Albertorio et al. | 606/232 |
| 2008/0091237 | A1 * | 4/2008 | Schwartz et al. | 606/232 |
| 2008/0103528 | A1 * | 5/2008 | Zirps et al. | 606/232 |
| 2008/0188893 | A1 * | 8/2008 | Selvitelli et al. | 606/232 |
| 2008/0195148 | A1 * | 8/2008 | Cook et al. | 606/232 |
| 2008/0234819 | A1 * | 9/2008 | Schmieding et al. | 623/13.14 |
| 2008/0255557 | A1 * | 10/2008 | Koyfman et al. | 606/60 |
| 2008/0262544 | A1 * | 10/2008 | Burkhart | 606/232 |
| 2008/0287991 | A1 * | 11/2008 | Fromm | 606/232 |
| 2008/0287992 | A1 * | 11/2008 | Tornier et al. | 606/232 |
| 2009/0054928 | A1 * | 2/2009 | Denham et al. | 606/232 |
| 2009/0182335 | A1 * | 7/2009 | Struhl | 606/60 |
| 2009/0275950 | A1 | 11/2009 | Sterrett et al. | |
| 2010/0114161 | A1 * | 5/2010 | Bojarski et al. | 606/223 |
| 2010/0114162 | A1 * | 5/2010 | Bojarski et al. | 606/228 |
| 2010/0125297 | A1 * | 5/2010 | Guederian et al. | 606/232 |
| 2010/0152752 | A1 * | 6/2010 | Denove et al. | 606/148 |
| 2010/0256677 | A1 * | 10/2010 | Albertorio et al. | 606/232 |
| 2010/0268232 | A1 * | 10/2010 | Betz et al. | 606/79 |
| 2010/0268273 | A1 * | 10/2010 | Albertorio et al. | 606/232 |
| 2010/0324676 | A1 * | 12/2010 | Albertorio et al. | 623/13.14 |
| 2010/0331612 | A1 * | 12/2010 | Lashinski et al. | 600/37 |
| 2011/0046734 | A1 * | 2/2011 | Tobis et al. | 623/13.14 |
| 2011/0118780 | A1 * | 5/2011 | Holmes, Jr. | 606/232 |
| 2011/0118781 | A1 * | 5/2011 | Cook et al. | 606/232 |
| 2011/0125189 | A1 * | 5/2011 | Stoll et al. | 606/232 |
| 2011/0130789 | A1 * | 6/2011 | Shurnas et al. | 606/232 |
| 2011/0137416 | A1 * | 6/2011 | Myers | 623/13.14 |
| 2011/0276137 | A1 * | 11/2011 | Seedhom et al. | 623/13.11 |
| 2012/0016386 | A1 * | 1/2012 | Bojarski et al. | 606/148 |
| 2012/0016415 | A1 * | 1/2012 | Green et al. | 606/232 |
| 2012/0041484 | A1 * | 2/2012 | Briganti et al. | 606/232 |
| 2012/0046746 | A1 * | 2/2012 | Konicek | 623/13.14 |
| 2012/0059469 | A1 * | 3/2012 | Myers et al. | 623/13.14 |
| 2012/0065731 | A1 * | 3/2012 | Justin et al. | 623/13.14 |
| 2012/0071896 | A1 * | 3/2012 | Ferree | 606/139 |
| 2012/0101526 | A1 * | 4/2012 | Bennett | 606/232 |
| 2012/0109156 | A1 * | 5/2012 | Overes et al. | 606/139 |
| 2012/0109194 | A1 * | 5/2012 | Miller et al. | 606/232 |

FOREIGN PATENT DOCUMENTS

| | | |
|---|---|---|
| EP | 1 889 575 A2 | 2/2008 |
| WO | WO 02/091959 A1 | 11/2002 |

* cited by examiner

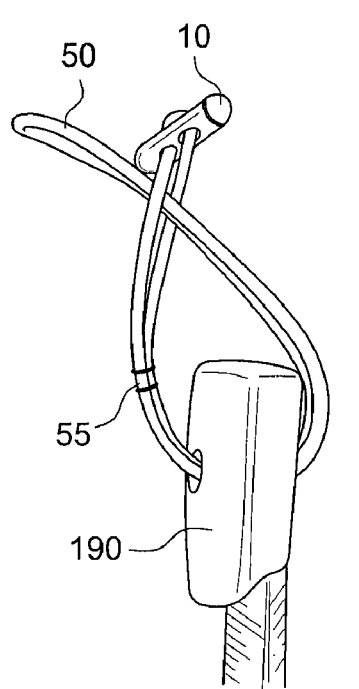
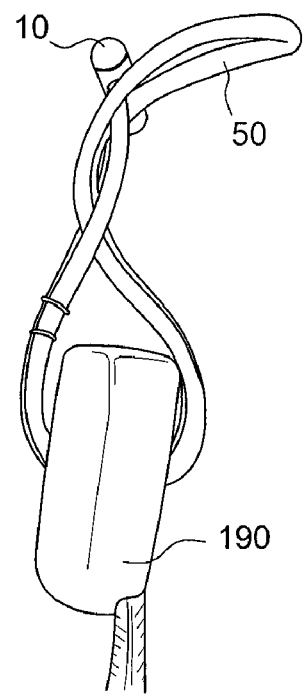
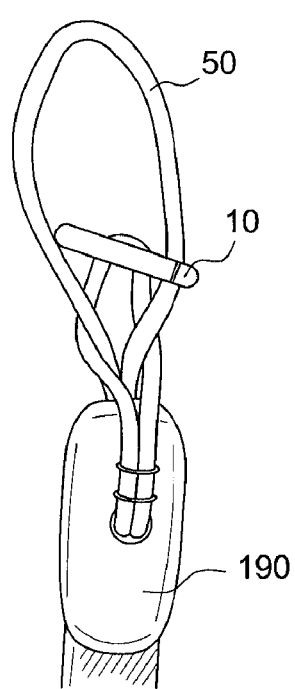
*FIG. 7(a)*     *FIG. 7(b)*     *FIG. 7(c)*
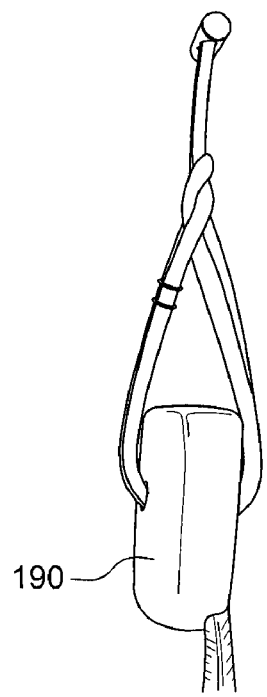
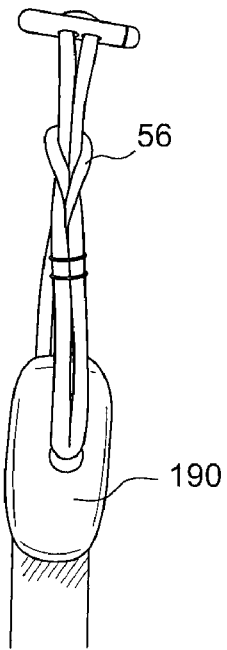
*FIG. 7(d)*     *FIG. 7(e)*

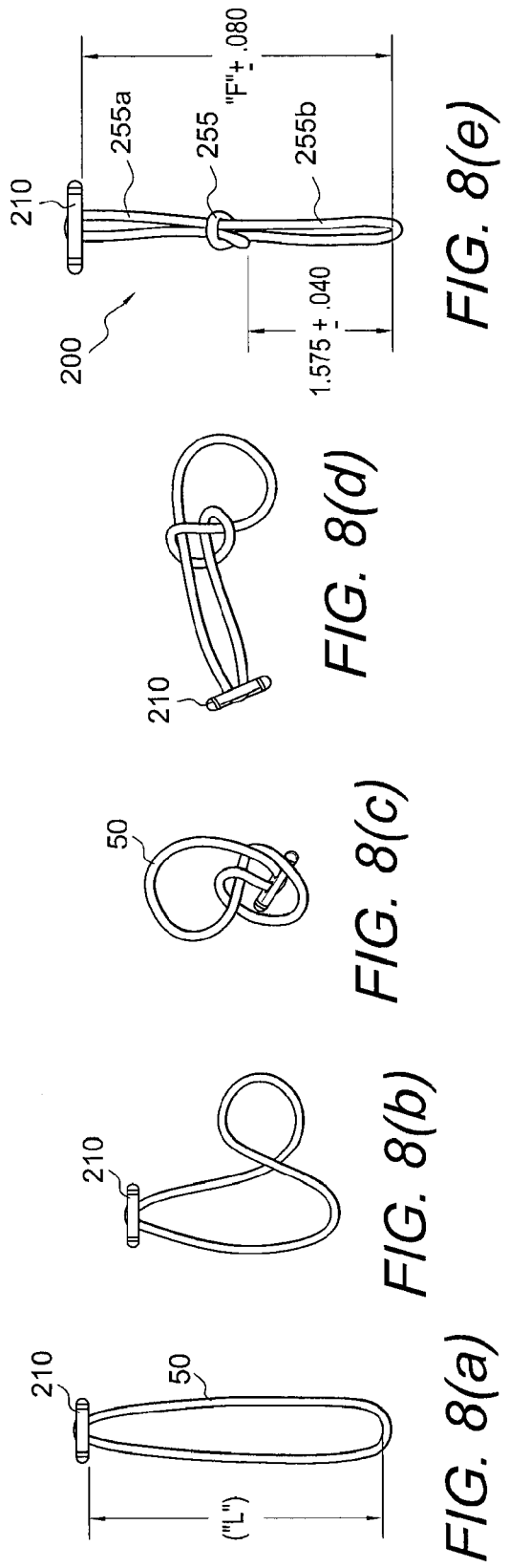

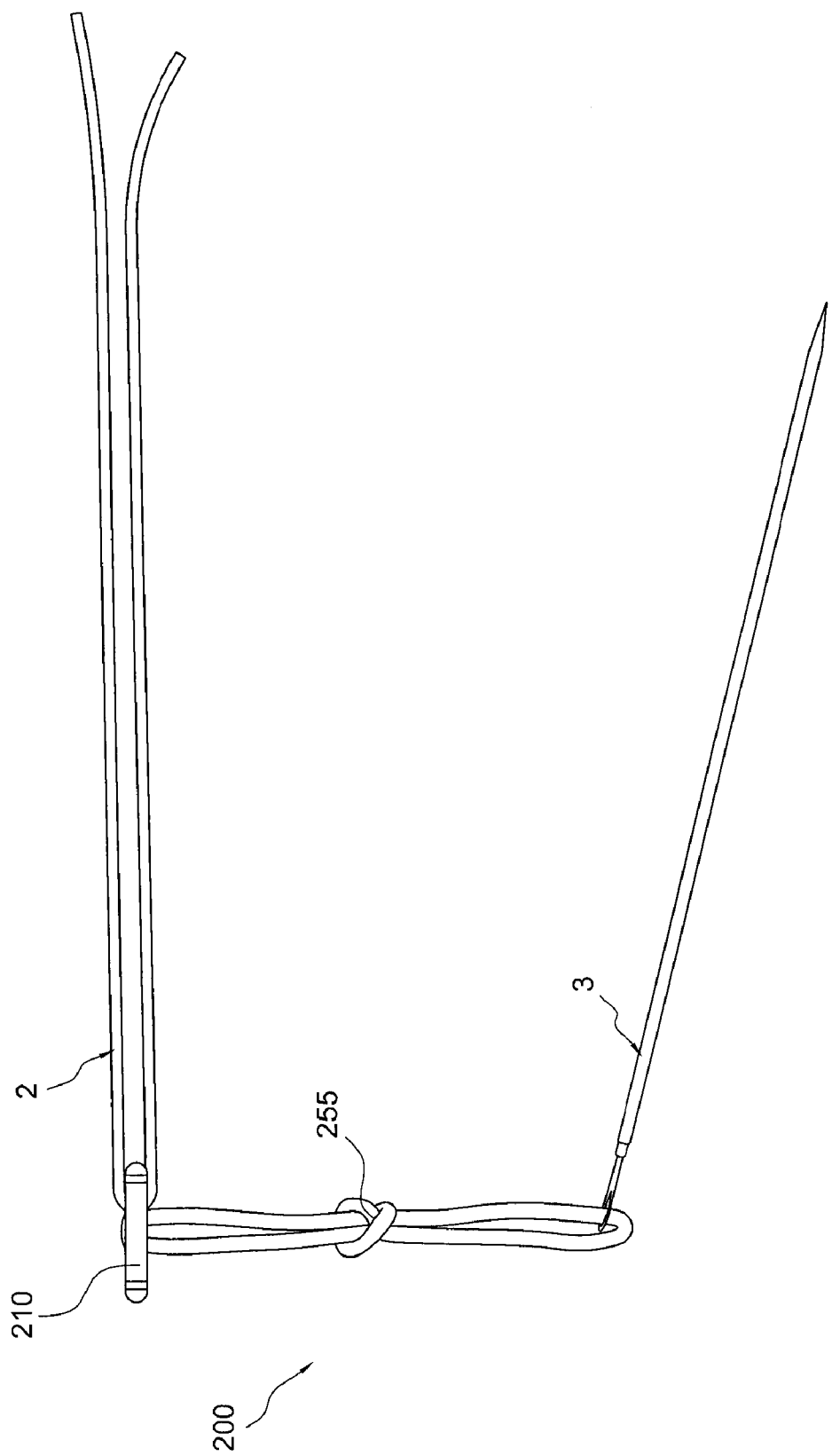

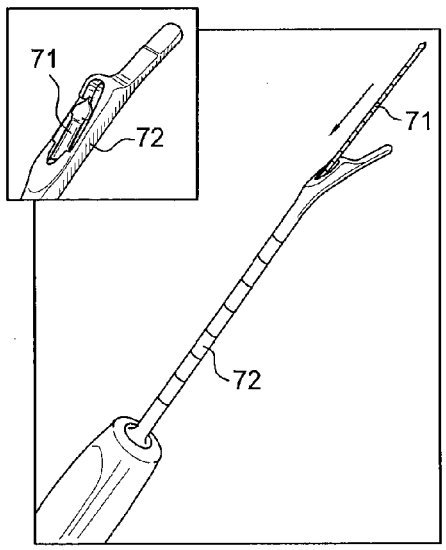
FIG. 13
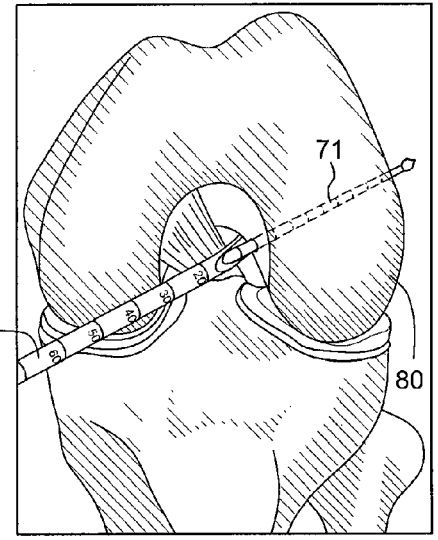
FIG. 14
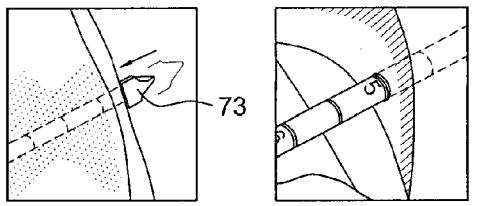
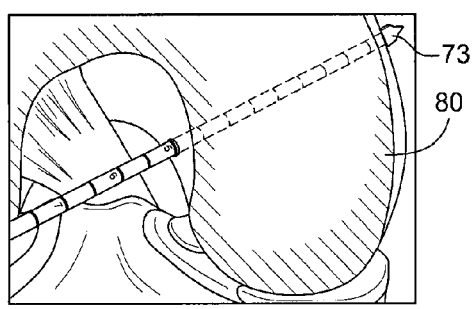
FIG. 15
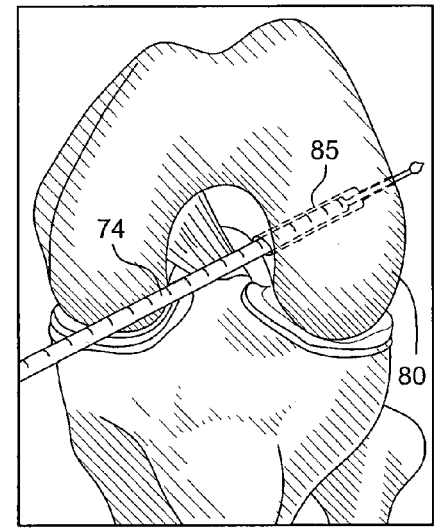
FIG. 16

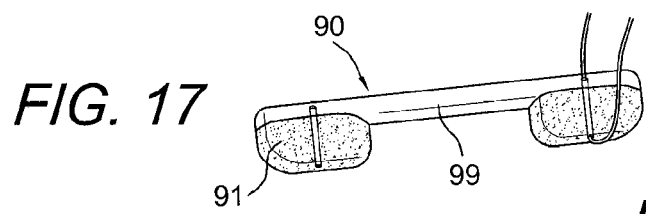
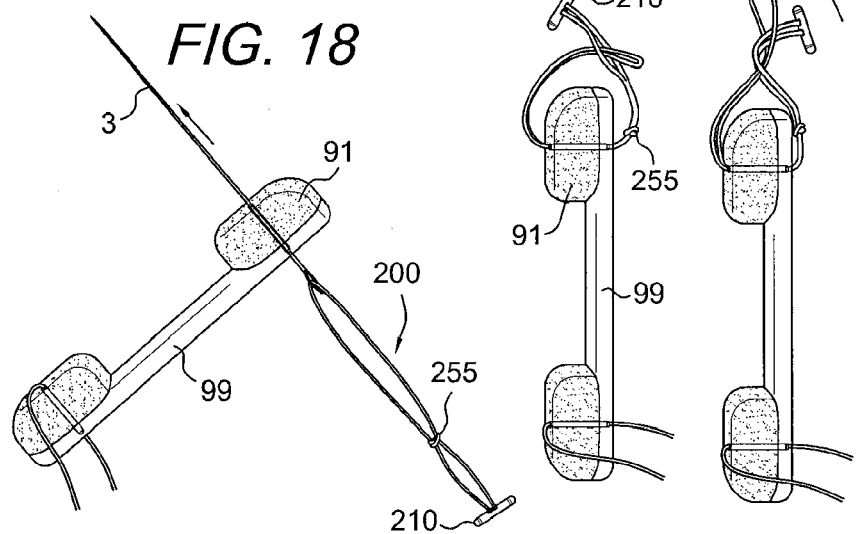
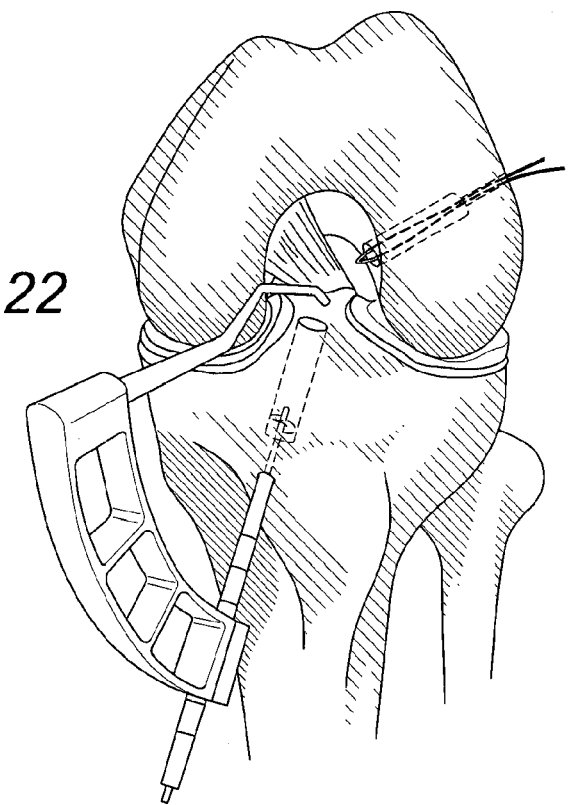
FIG. 17
FIG. 18
FIG. 19
FIG. 20
FIG. 21
FIG. 22

BONE-TENDON-BONE SUTURE BUTTON CONSTRUCTS AND METHODS OF TISSUE FIXATION

CROSS-REFERENCE TO RELATED APPLICATIONS

This application claims the benefit of U.S. Provisional Application Ser. No. 61/218,833, filed Jun. 19, 2009, the entire disclosure of which is incorporated by reference herein.

FIELD OF THE INVENTION

The present invention relates to the field of surgery reconstruction and, more particularly, to joint or ligament reconstruction techniques and associated fixation and reconstruction devices.

BACKGROUND OF THE INVENTION

Reconstructive surgeries, particularly anterior cruciate ligament (ACL) reconstruction, are well-known in the art. Methods of ACL reconstruction using interference screw fixation are described, for example, in U.S. Pat. Nos. 5,211,647 and 5,320,626. In general, these methods of tenodesis involve drilling a tunnel through the tibia, drilling a closed tunnel (socket) into the femur, inserting a substitute ACL graft into the tunnels, and securing the grafts to the walls of the tibial and femoral tunnels using interference screws or the like.

Other methods of ACL reconstruction include using a button/loop construct for fixation, such as disclosed in U.S. Pat. No. 6,533,802 and U.S. Patent Application Publication No. 2008/0046009. An exemplary method of using a button/loop construct includes the steps of drilling a bone tunnel in an antegrade or retrograde manner, securing a graft (soft tissue or bone-tendon-bone (BTB) graft) to the button/loop construct, passing the graft with button through the bone tunnel, and securing the button to the bone cortex once the button exits the bone tunnel.

The devices and methods of ligament reconstruction of the present invention provide an alternative reconstruction system that employs a fixation device such as a button with a flexible loop attached to a BTB graft, the flexible loop having at least one joined region which may be a bridge of material, a pre-formed knot, a bond or a stitch provided distal to the button, for reproducible graft attachment and improved fixation, graft protection and insertion technique.

SUMMARY OF THE INVENTION

The present invention provides techniques and reconstruction systems for ligament repair and fixation, including bone to bone, or soft tissue to bone. The reconstruction system of the present invention comprises a fixation device (for example, a button) with a closed loop of flexible material attached to the fixation device. The closed loop is provided with at least one joined region (a bridged, stitched, bonded or knotted region) to form a closed loop figure-8 construct with proximal and distal openings with respect to the fixation device. The figure-8 construct (either bridged, stitched, bonded or knotted) may be attached to a bone block of a BTB graft, for example, and used for ligament reconstruction.

These and other features and advantages of the invention will be more apparent from the following detailed description that is provided in connection with the accompanying drawing and illustrated exemplary embodiments of the invention.

BRIEF DESCRIPTION OF THE DRAWINGS

FIGS. 7(a)-(e) illustrate subsequent steps of attaching the reconstruction system of FIG. 1 to a bone block.

FIGS. 8(a)-(e) illustrate subsequent steps for the formation of a reconstruction system (a knotted loop/button construct) according to a second exemplary embodiment of the present invention (with an exemplary 12 mm button).

FIGS. 9 and 9(a) illustrate a reconstruction system (a knotted loop/button construct) according to a second embodiment of the present invention (with an exemplary 12 mm button).

FIGS. 10-25 illustrate subsequent steps for femoral ACL reconstruction using a button and employing a BTB graft attached to the reconstruction system (knotted loop/button construct) of FIGS. 9 and 9(a).

DETAILED DESCRIPTION OF THE PREFERRED EMBODIMENTS

The present invention provides a reconstruction system for ligament repair and insertion technique that employs a fixation device such as a button with a closed loop of flexible material. The closed loop is provided with at least one joined region (a bridged, stitched or bonded region, or a knotted region) to form a closed loop having a figure-8 configuration construct. The figure-8 construct (either bridged, stitched, bonded or knotted) may be attached to a bone block of a BTB graft, for example, and used for ligament reconstruction.

According to an exemplary embodiment, the reconstruction system of the present invention comprises a fixation device (for example, a button) with a closed loop of flexible material attached to the fixation device (button) and to a BTB graft. The closed loop with attached button is knotted, bridged, stitched or bonded together below the button (for example, about 15 mm below the button) to form a construct having a "figure 8" configuration. The distal loop of the figure-8 construct is passed through the bone block of the BTB graft, then through the proximal loop of the figure-8, and then over the button. The distal loop is then pulled and cinched down over the joined region (bridged, stitched, bonded or knotteed section). The resulting BTB button construct provides reproducible placement of the BTB graft.

Figure 9A:
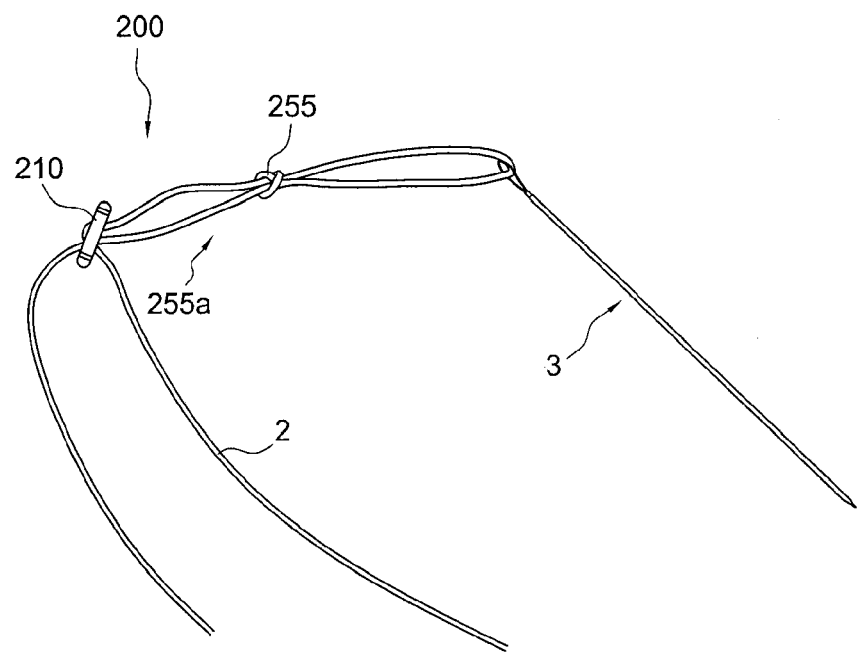
Figures 9B, 9C, 9D:
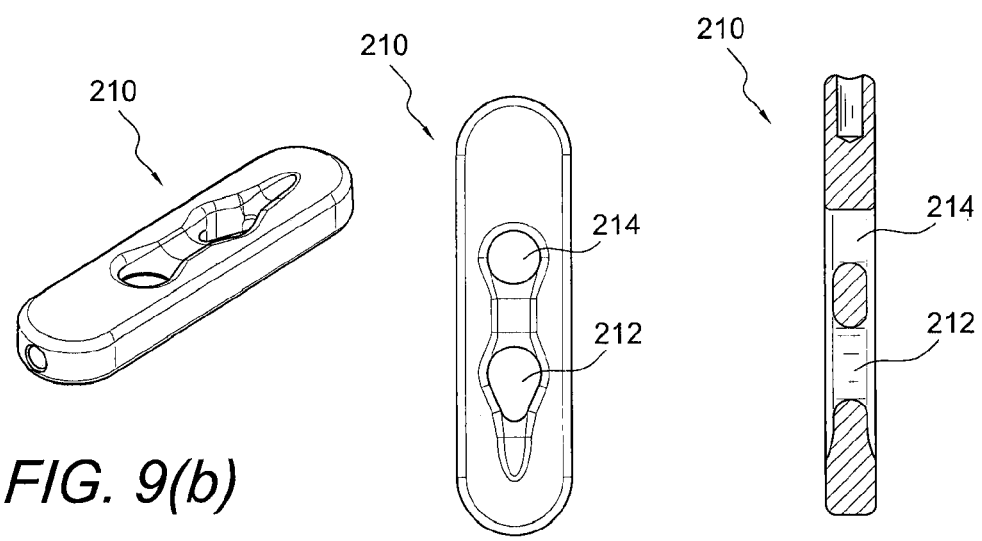
FIGS. 9(b), 9(c), and 9(d) show details of the button.
Figure 10:
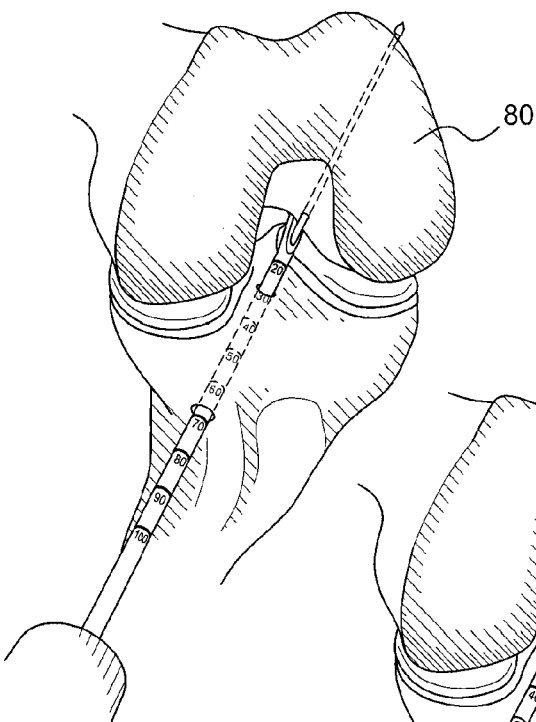
Figure 11:
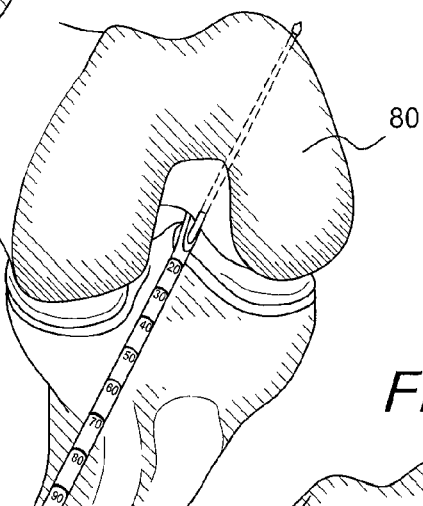

According to another exemplary embodiment, the closed flexible loop with attached button is provided with at least one knotted section (at least one knot) distal to the button, to form a knotted loop construct having a "figure 8" configuration. The knotted loop construct may be provided to the surgeon with the knotted region already formed or may be formed by the surgeon. The closed flexible loop is first configured into a "figure 8" shape, by twisting a portion of the closed loop to create a small and a large loop distal to the button. The button is passed through the small loop to form the knotted joined region (the knot). The steps for creating the knotted region are illustrated in FIGS. 8A-E. The distal loop of the figure-8 construct is passed through the bone block of the BTB graft, through the proximal loop of the figure-8, and then over the button. The distal loop is then pulled and cinched over the pre-formed knot. A needle may be assembled to the construct to ease insertion through the bone block as shown in FIG. 9.

The present invention also provides a method of ligament repair including fixation of bone to bone, or soft tissue to bone. The method of the present invention comprises the steps of: (i) providing a tunnel or socket from a first bone surface and to a second bone surface; (ii) providing a reconstruction system including a fixation device such as a button joined to a graft by a closed loop of flexible material having at least one joined region (a bridged, stitched, bonded or knotted section) below the button, in the vicinity of the bone surface; (iii) advancing the button from the first bone surface until it exits the second bone surface; and (iv) securing the graft within the bone tunnel.

Referring now to the drawings, where like elements are designated by like reference numerals, FIGS. 1-9 illustrate various embodiments of the reconstruction system 100, 200 of the present invention comprising a flexible closed loop provided with at least one joined section (a bridged, stitched, bonded or knotted region) and connected to a fixation device (for example, a button). FIGS. 10-25 illustrate exemplary steps for femoral ACL reconstruction using a button and employing a BTB graft attached to the reconstruction system 200 (a knotted loop/button construct) of FIGS. 9 and 9(*a*).

Figure 3:
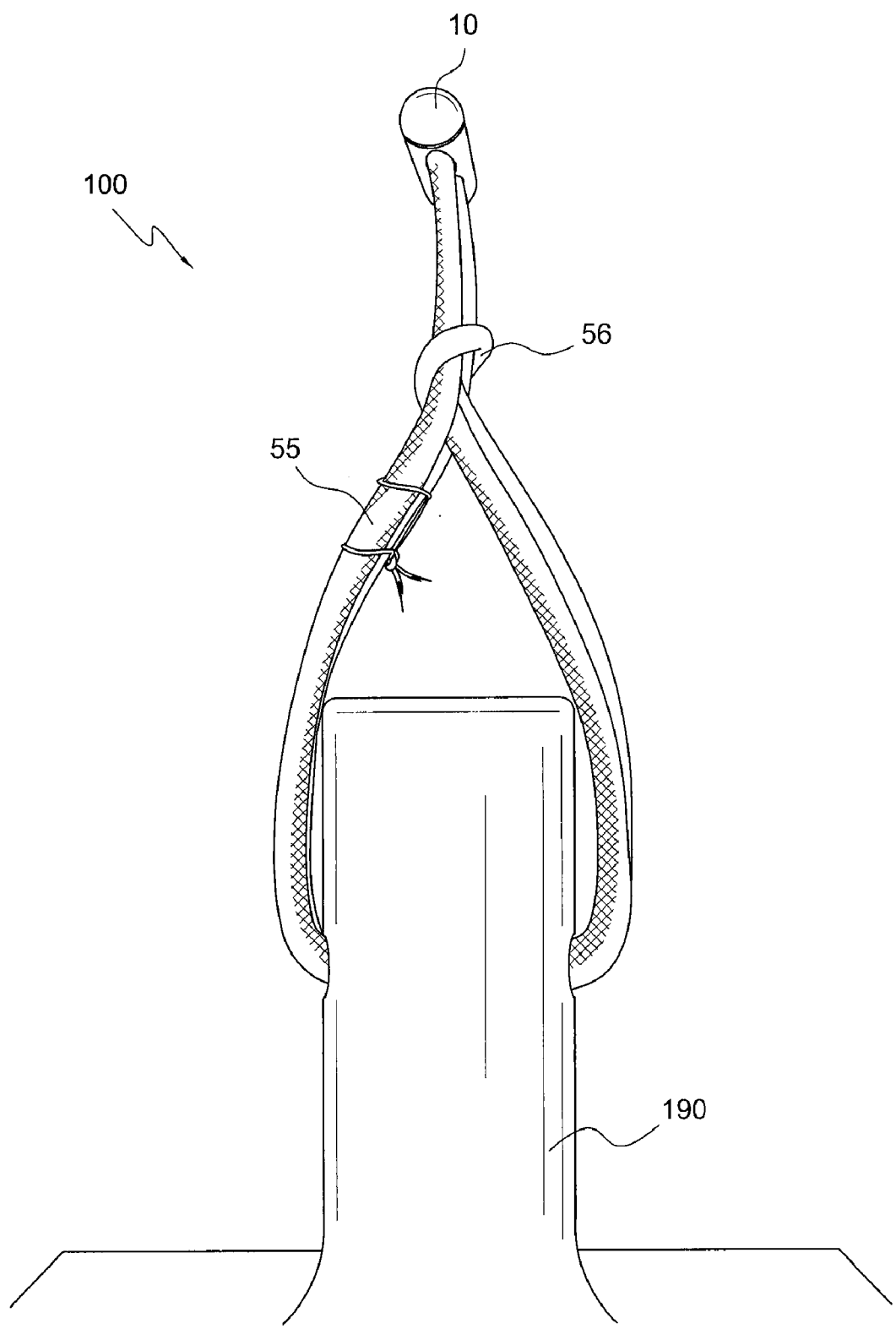
FIG. 3 illustrates the reconstruction system of FIG. 1 attached to a bone block.
Figure 4:
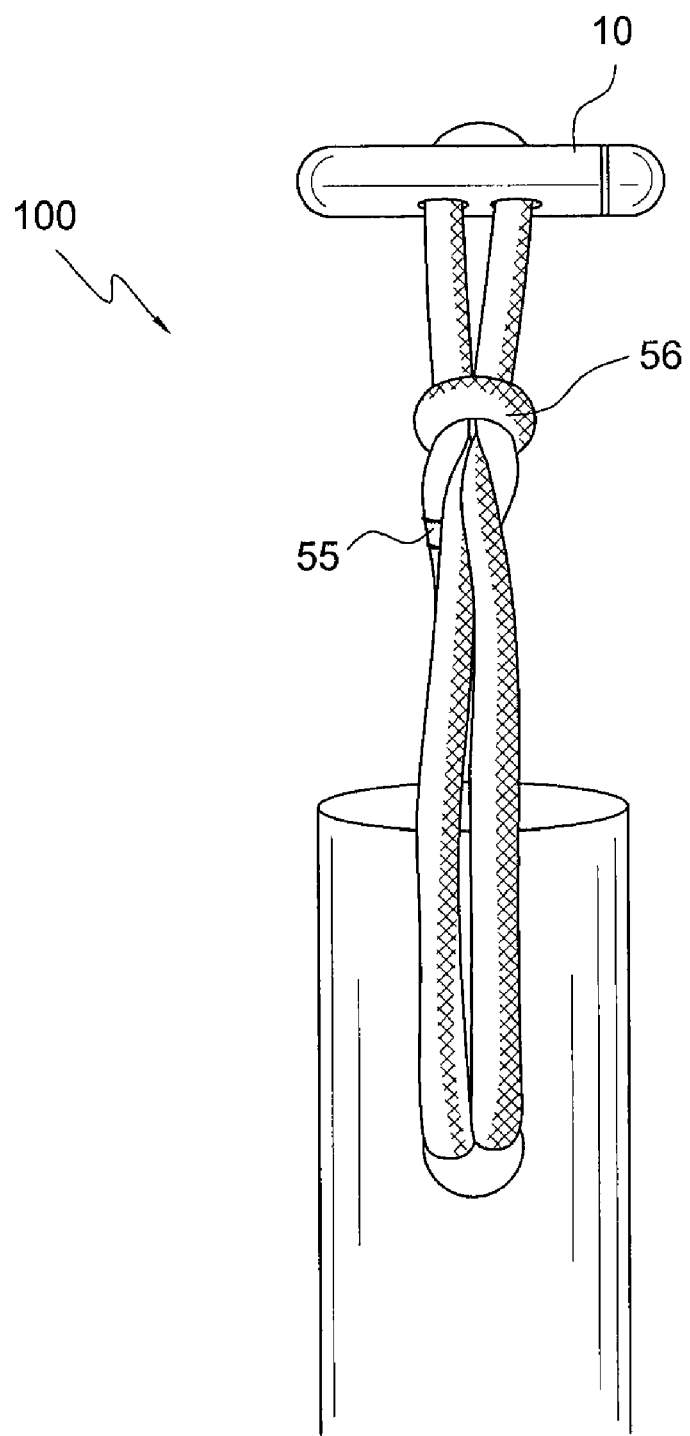
FIG. 4 illustrates a side view of the reconstruction system of FIG. 3 attached to the bone block.

FIGS. 1-7 illustrate a reconstruction system 100 according to a first exemplary embodiment of the present invention and comprising a fixation device 10 (for example, a button 10), a closed flexible loop 50 and a bone block 190 with a ligament graft. Ligament graft may be autograft, allograft or artificial graft. The flexible loop 50 is connected to the fixation device 10 and may be attached to the bone block 190 at the time of surgery or prior to the surgery. FIGS. 4 and 7 illustrate the reconstruction system 100 with bone block 190 attached.

Figure 1:
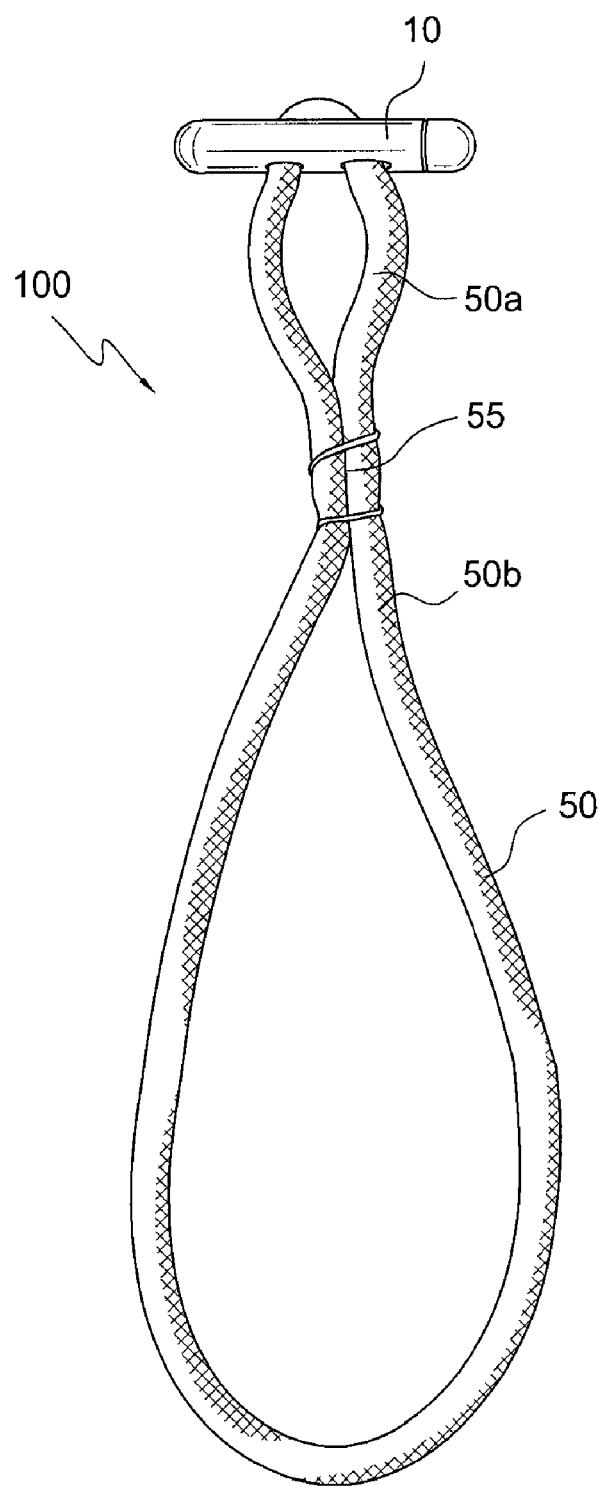
FIG. 1 illustrates a reconstruction system (a figure-8 loop with stitched joined region/button construct) according to a first exemplary embodiment of the present invention.
Figure 2:
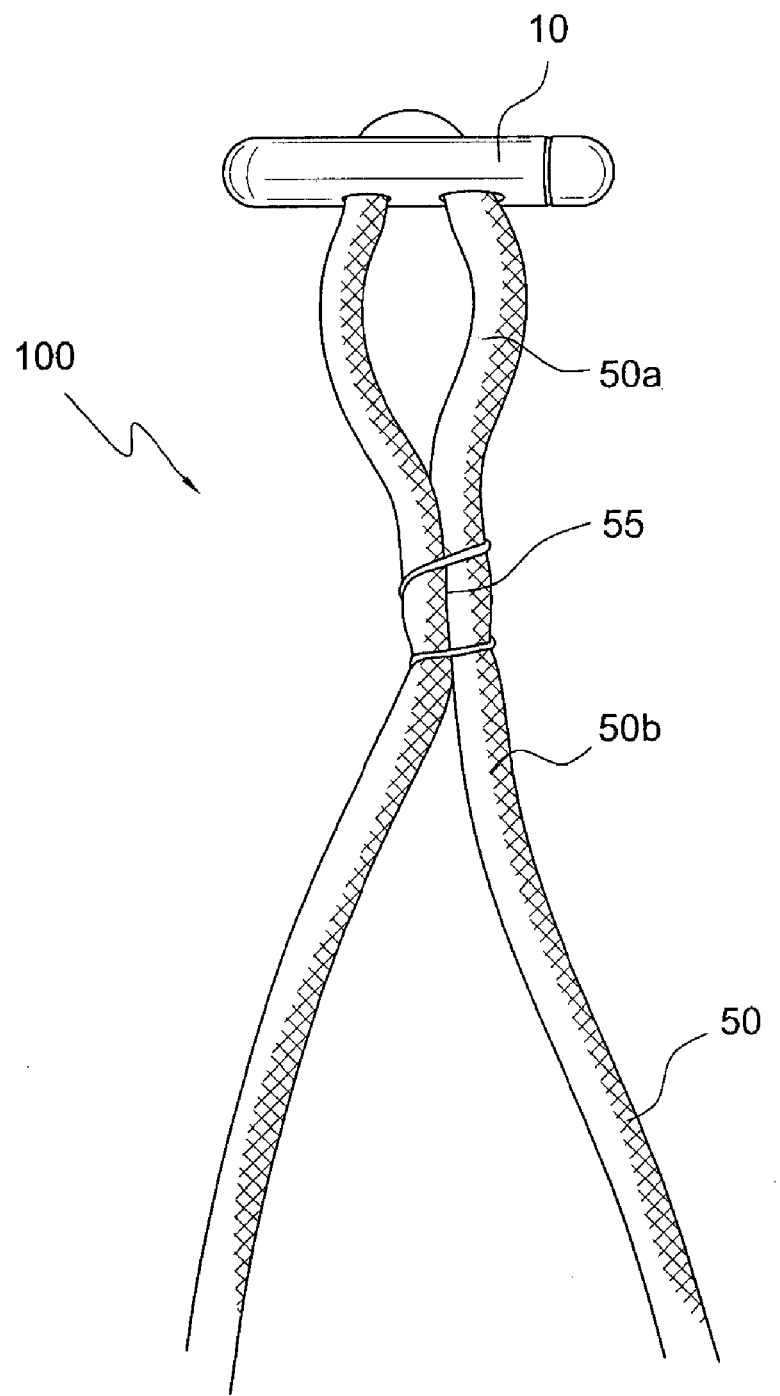
FIG. 2 illustrates an enlarged view of the button and of the proximal loop of the reconstruction system of FIG. 1 prior to attachment to the bone block.

Closed flexible loop 50 of reconstruction system 100 is provided with at least one connection region 55 which may be bridged, stitched, bonded or knotted, as shown in FIGS. 1-7. In an exemplary embodiment, the closed loop 50 the joined region is bridged, stitched or bonded together in at least one region below the button 10 to a distance of about 10 mm to about 15 mm, to form the loop construct having a "figure 8" configuration (as shown in FIG. 1, for example). The exemplary loop construct having a "figure 8" configuration (FIG. 1) comprises a proximal closed loop 50*a* (having a first perimeter) adjacent a distal closed loop 50*b* (having a second perimeter). The first and second perimeters of the proximal and distal loops 50*a*, 50*b* may be similar or different. The joined region 55 separates the proximal and distal loops 50*a*, 50*b*.

FIGS. 3 and 4 illustrate the reconstruction system 100 of FIG. 1 with distal loop 50*b* of the figure-8 construct attached to the bone block 190 of the BTB graft. The figure-8 construct is attached to the BTB graft as shown in FIGS. 7A-E. The distal loop 50*b* is passed through the bone block 190, then through the proximal loop 50*a* of the "figure 8" construct, and then over the button 10 and pulled. The distal loop 50*b* is then cinched over the connection region (bridged, stitched or bonded) 55 to form knot 56. Providing the joined region 55 distal to the button 10, allows for cinching of the distal loop to occur away from the bone block 190, increasing strength and making sizing more consistent. The joined region 55 prevents the distal loop from tightening or constricting on the bone block 190 when a load or tension is applied, providing a more secure, protected graft for implantation. The placement of the joined region 55 at the same place in each construct allows for the distance of the bone block to be set at a known distance each time. The distal loop perimeter is a constant while the proximal loop perimeter may be changed depending on the size of the desired reconstruction system. The BTB button construct provides reproducible graft attachment.

Figure 5:
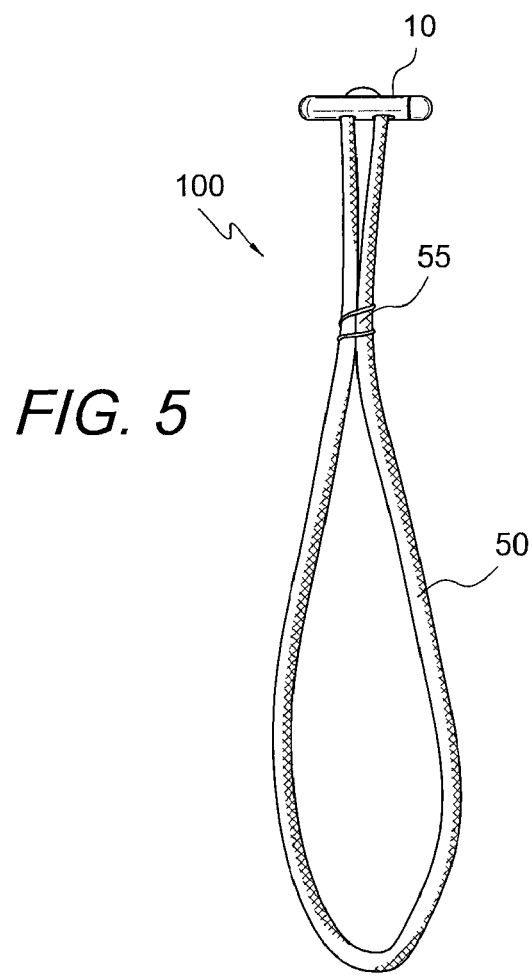
FIG. 5 illustrates another view of the reconstruction system of FIG. 1 prior to bone block attachment.
Figure 6:
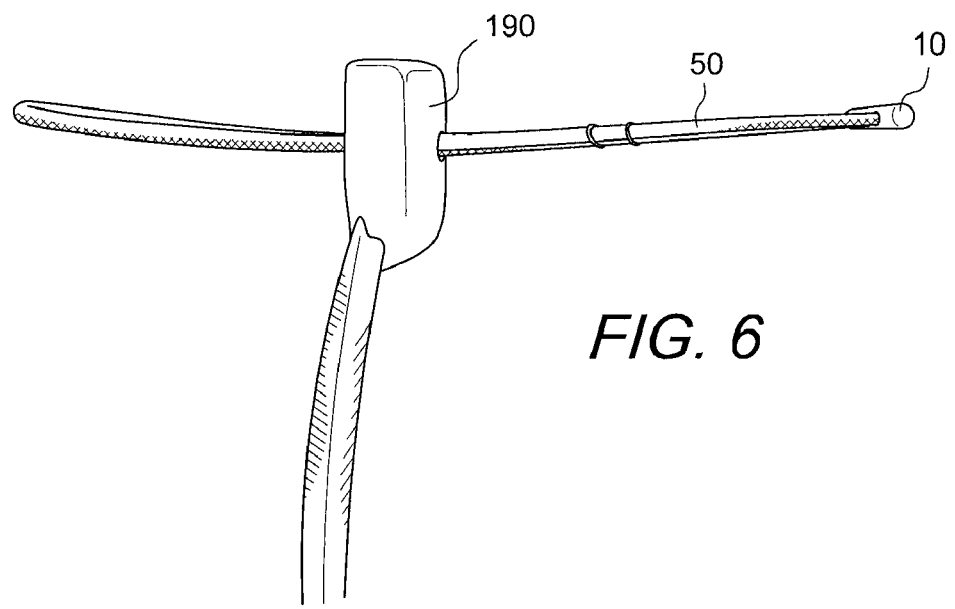
FIG. 6 illustrates another view of the reconstruction system of FIG. 5 passing through the bone block prior to attachment.

FIG. 5 illustrates the loop connected just below the button 10. This allows "cinching" of the loop to take place away from the bone block 190, increasing strength and making sizing more consistent. FIG. 6 illustrates loop 50 which is very thin to ease passage through a hole in the bone block. FIGS. 7(*a*)-(*e*) illustrate exemplary, subsequent steps of attaching the reconstruction system of FIG. 1 to a bone block 190. The loop 50 is passed through the bone block 190 and back through the loop 50 (above the connected portion). The loop 50 is then passed over the button 10. Knot 56 is then cinched down and "bottoms out" on the connected portion of the loop.

FIGS. 8(*a*)-(*e*) illustrate another exemplary embodiment of a reconstruction system 200 of the present invention comprising a fixation device 210 (for example, a button) and a flexible closed loop 50 provided with at least one connection region in the form of a knotted section 255. The steps shown in FIGS. 8(*a*)-(*e*) comprise inter alias providing a button attached to a continuous, uninterrupted flexible loop (FIG. 8(*a*)); creating a "figure-8" construct (with a small loop and a large loop) (FIG. 8(*b*)); passing the button through the small loop (FIG. 8(*c*)); tightening the knot (FIG. 8(*d*)); and inspecting the dimensions of the final construct (FIG. 8(*e*))

FIGS. 9 and 9(*a*) illustrate the reconstruction system 200 of FIG. 8 with a passing suture 2 and a needle 3 with a nitinol loop attached to the reconstruction system 200 for insertion. In this exemplary embodiment only, the fixation device 210 may be a 12 mm or a 15 mm RetroButton sold by Arthrex, Inc of Naples, FL, and disclosed in U.S. Patent Application Publication No. 2008/0046009.

FIGS. 10-25 illustrate exemplary subsequent steps for femoral ACL reconstruction using a button and employing a BTB graft attached to the reconstruction system (a knotted loop/button construct) of FIGS. 9 and 9(*a*).

Figure 12:
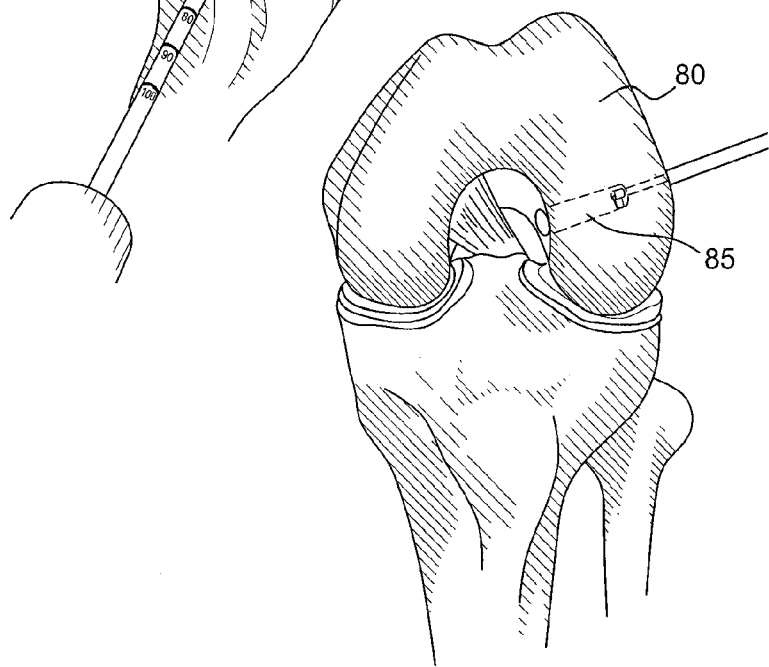

The system of the present invention provides freedom in anatomic ACL reconstruction. The versatile button used in the present invention is compatible with several approaches to ACL reconstruction. The femoral socket may be prepared through the tibial tunnel (FIG. 10), the anteromedial portal (FIG. 11) or outside/in, using a retrograde cutter (FIG. 12).

The AM portal approach will be described below. A femoral socket may be drilled transtibially through the medial portal or by a retrograde technique using a retrograde cutter such as an Arthrex FlipCutter®, disclosed in U.S. Patent Application Publication No. 2009/0275950, the disclosure of which is incorporated by reference in its entirety herewith. In a medial portal option, for medial portal and transtibial drilling, a drill pin such as an Arthrex RetroButton® Drill Pin may be used. As detailed below, the intraosseous distance is noted by pulling back on the pin by hand, until it catches the femoral cortex. The depth marking are read on the pin closest to the femoral notch.

Femoral Socket Preparation (FIGS. 13-16)

FIGS. 13 and 14: A drill pin, such as an Arthrex RetroButton® Drill Pin, is loaded in an ACL drill pin guide, such as an Arthrex Transportal ACL Guide (TPG) 72. The drill guide 72 is advanced through the medial portal and into position. The knee is flexed to approximately 110° and the drill pin 71 is drilled through femur 80 until it exits the lateral cortex.

FIGS. 15 and 16: The drill pin guide 72 is removed from the drill pin 71 and the drill pin is pulled until the enlarged tip 73 engages the lateral cortex. The intraosseous length is noted via arthroscopic viewing (in the exemplary case, the length is about 50 mm).

Using a cannulated reamer 74 (about 0.5 mm to 1 mm larger than the diameter of the graft), the femoral socket 85 is reamed to a distance about 10 mm longer than the amount of graft desired in the socket (example: for a 20 mm of graft, drill a socket at least 30 mm deep). A flexible strand (preferably formed of a high strength suture, such as 2 Arthrex FiberWire® suture) is passed using the eyelet in the drill pin 71.
Graft Preparation, Button Sizing and Graft Attachment (FIGS. 17-22)

FIG. 17 illustrates a BTB graft 90. The femoral bone block 91 is preferably about 20 mm long and at least 9 mm in diameter. A hole 92 is drilled of about 2.4 mm in a direction about perpendicular to the cortex, 10 mm distal to the proximal end.

A loop is chosen that is 15 mm shorter than the intraosseous length. In this example, the intraosseous length is about 50 mm (50−15=35, so a 35 mm loop should preferably be used).

Figure 23:
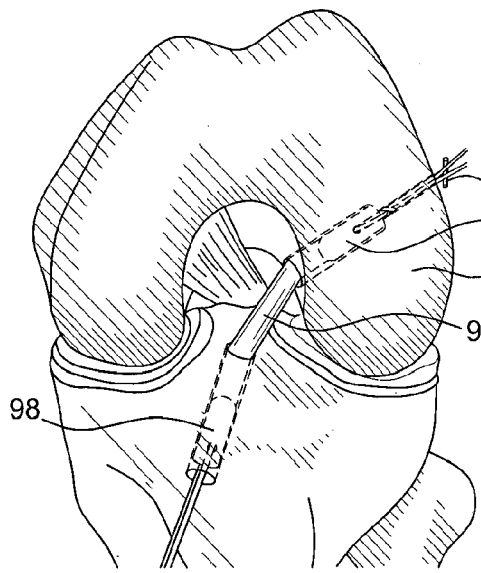
Figure 24:
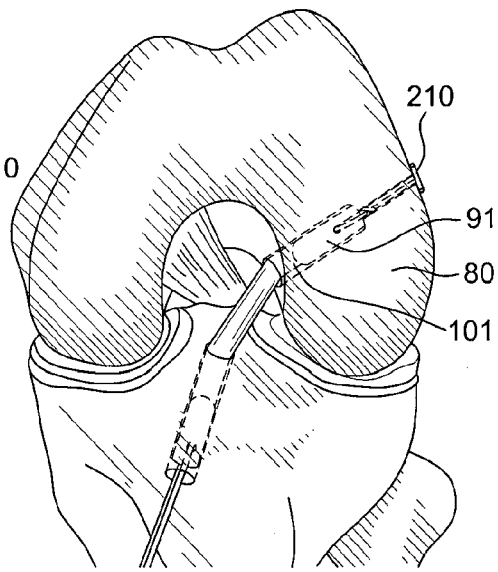
Figure 25:
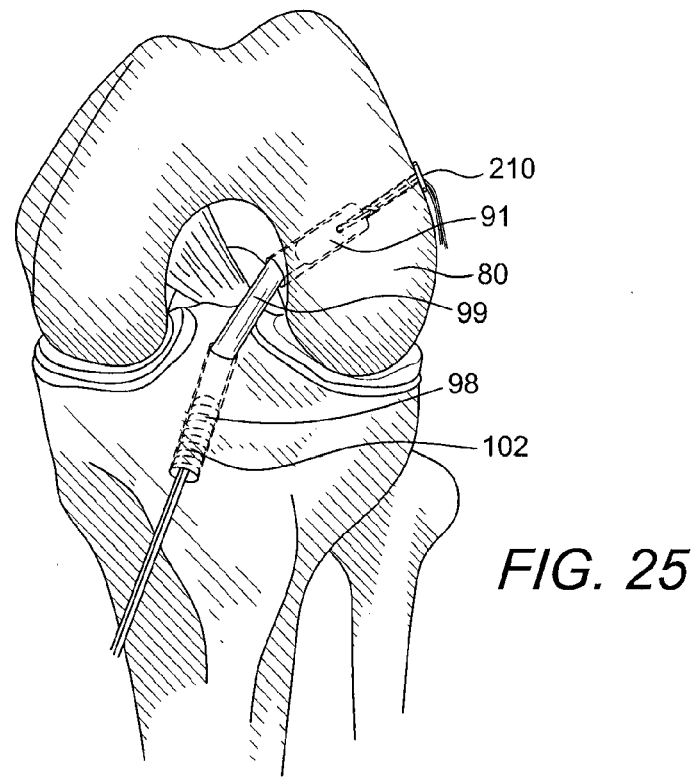

The needle 3 attached to the loop 250 is passed through the drill hole 92 in the bone block 91. The needle is cut off the loop and the loop is passed between loop strands, under the button 210. The loop is placed over the button 210 and cinched down to form another knot 260 (FIG. 21). The graft 99 is marked to match the length of the femoral socket 85. The tibia tunnel or socket may then be prepared (for example, by retrograde drilling).
Graft Passing (FIGS. 23-25)

If a complete tibial tunnel 65 has been formed, the femoral passing suture is retrieved through the tibial tunnel. For "all-inside" ACL reconstruction, the graft must be passed through the medial portal. The button sutures 2 are placed in the femoral passing suture and pulled out of the lateral thigh. The button 210 should be oriented with the nonlooped portion facing lateral. The button sutures 2 are pulled to pass the button 210 and graft 99. The graft should be pulled into the tunnel until the mark reaches the femoral socket, signaling that the button 210 has exited the femur 80.

Aperture fixation may be obtained by placing a fixation device 101 (for example, an interference screw) into the femoral socket. Tibial fixation may then be carried out with another fixation device 102, such as a bioabsorbable interference screw, distally.

The system of the present invention allows stronger and simpler ACL graft fixation. The 12 mm titanium button 210 of the present invention passes through a guide pin hole to preserve cortical bone for enhanced cortical bone fixation and eliminates the need for overdrilling with larger diameter cannulated drills. Advantageously, the button of the present invention is self-flipping.

In the above-described embodiments, the fixation device or button 10, 210 is preferably connected to the flexible closed loop 50 as detailed and described in U.S. Patent Application Publication No. 2008/0046009, the disclosure of which is incorporated by reference in its entirety herewith. As detailed in FIGS. 9(*b*), 9(*c*) and 9(*d*) of the present application, the button 10, 210 is provided with a pair of openings that allows the passage of the flexible material 50. Since the button of the present invention is self-flipping, no trailing suture is necessary, and, in a preferred embodiment, the button is provided with one oval hole 212 (to accommodate both the strand of closed loop 50 and the button suture 2, and a round hole 214 (to accommodate only the strand of closed loop 50). The button 10, 210 may be formed, for example, of metal, PEEK or PLLA, absorbable or nonaborbable, natural or synthetic polymers, ceramic, bone, or any combination thereof The flexible material 50 may be a absorbable or nonabsorbable, natural or synthetic, monofilament strand, multifilament strand, a braid or a high strength suture such as FiberWire® suture, sold by Arthrex, Inc. of Naples, Fla., or any combination thereof The flexible material is threaded through the fixation device 10, 210 to create flexible loop 50.

The flexible material 50 may be also suture such as a suture braid with braided filaments having a hollow core (for example, strands of suture such as ultrahigh molecular weight polyethylene (UHMWPE) braided with strands of polyester, collagen, or other suture materials, such as PET, PEEK, silk nylon, and absorbable polymers, among many others). The flexible material 50 may also contain a bioabsorbable material, such as PLLA or one of the other polylactides, for example, and/or may be formed of twisted fibers having strands of a contrasting color added to the braided threads, to make the suture more visible during surgical procedures. If desired, the flexible material 50 may be coated (partially or totally) with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the braid, knot security, pliability, handleability or abrasion resistance, for example.

The reconstruction system 100, 200 of the present invention may be introduced into a socket/tunnel in the femoral side of the knee (usually through an arthroscopic portal). The fixation device 10, 210 or button and the portion of the closed loop connected to the button are pulled out of the bone cortex with the passing sutures (later discarded). Upon exiting the hole in the bone cortex, the button, closed loop and passing sutures decompress, securing the button against the surface of the bone and fixing the construct in place. The graft (attached to bone blocks 91, 98, for example) is advanced further into the femoral and tibial sockets/tunnels and secured with additional fixation devices (such as interference screws, for example) to the walls of the sockets/tunnels, as is known in the art.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. An assembled bone-tendon-bone graft for use in surgical procedures, comprising: a graft attached to a first bone block and a second bone block; a button/loop construct attached to one of the first and second bone blocks, the button/loop construct comprising a button and a continuous flexible loop attached to the button, the flexible loop having a knotted region that divides the flexible loop into a proximal loop and a distal loop relative to the button; a needle attached to the distal loop; and at least one passing suture attached to the button.

2. The assembled bone-tendon-bone graft of claim 1, wherein the flexible loop is formed of a high strength suture material.

3. The assembled bone-tendon-bone graft of claim 1, wherein the button/loop construct is attached to one of the first and second bone blocks by passing the needle and the loop through a hole in one of the first and second bone blocks, and then passing the loop in between loop strands and under the button, and placing the loop over the button and cinching down to form another knot.

4. The assembled bone-tendon-bone graft of claim 1, wherein the needle is a nitinol needle.

5. The assembled bone-tendon-bone graft of claim 1, wherein the needle and the at least one passing suture are pre-assembled to the graft and the button/loop construct prior to surgery.

6. The assembled bone-tendon-bone graft of claim 1, wherein the needle and the at least one passing suture are assembled to the graft and the button/loop construct by medical personnel, during surgery.

7. A method of ACL reconstruction, the method comprising the steps of:
   providing a bone-tendon-bone graft comprising a first bone block and a second bone block attached to a graft;
   providing a button/loop construct comprising a button; a continuous flexible loop attached to the button, the flexible loop having a first joined region; a needle attached to the button; and a passing suture attached to the flexible loop;
   attaching the button/loop construct to one of the first and second bone blocks by passing the needle with the attached loop through a hole formed within one of the first and second bone blocks, removing the needle off the loop and passing the loop between loop strands and under the button; placing the loop over the button, and cinching down to secure the loop to the bone block; and
   fixating the bone-tendon-bone graft with the button/loop construct within femur and tibia.

8. The method of claim 7, wherein the step of fixating the bone-tendon-bone graft with the button/loop construct within the femur and the tibia further comprises the steps of:
   forming a femoral socket and a tibial socket;
   advancing the button with one of the first and second bone blocks through the femoral socket, so that the button exits the femur and pivots and engages a cortical surface of the femur; and
   fixating the other of the first and second bone blocks within the tibial socket.

* * * * *